US012765925B2

(12) United States Patent
Zander

(10) Patent No.: US 12,765,925 B2
(45) Date of Patent: Oct. 20, 2026

(54) RETROGRADE NAIL WITH BONE PLATE

(71) Applicant: Stryker European Operations Limited, Carrigtwohill (IE)

(72) Inventor: Nils Zander, Eckernförde (DE)

(73) Assignee: Stryker European Operations Limited, Carrigtwohill (IE)

( * ) Notice: Subject to any disclaimer, the term of this patent is extended or adjusted under 35 U.S.C. 154(b) by 416 days.

(21) Appl. No.: 18/138,964

(22) Filed: Apr. 25, 2023

(65) Prior Publication Data

US 2023/0338070 A1 Oct. 26, 2023

Related U.S. Application Data

(60) Provisional application No. 63/334,855, filed on Apr. 26, 2022.

(51) Int. Cl.

| | |
|---|---|
| ***A61B 17/74*** | (2006.01) |
| ***A61B 17/80*** | (2006.01) |
| ***A61B 17/86*** | (2006.01) |

(52) U.S. Cl.

CPC ............ *A61B 17/744* (2013.01); *A61B 17/80* (2013.01); *A61B 17/86* (2013.01)

(58) Field of Classification Search

CPC ... A61B 17/744; A61B 17/746; A61B 17/748; A61B 17/80

USPC ......................................... 606/62, 64, 65, 67

See application file for complete search history.

(56) References Cited

U.S. PATENT DOCUMENTS

| | | | | |
|---|---|---|---|---|
| 4,667,663 A | | 5/1987 | Miyata | |
| 5,766,174 A | | 6/1998 | Perry | |
| 6,932,818 B2 | * | 8/2005 | Behrens | A61B 17/1725 606/64 |
| 8,734,448 B2 | * | 5/2014 | Thakkar | A61B 17/744 606/68 |
| 9,066,764 B2 | | 6/2015 | Perez | |
| 9,486,261 B2 | | 11/2016 | Plecko et al. | |
| 10,874,520 B2 | | 12/2020 | Segina et al. | |
| 2007/0123874 A1 | | 5/2007 | Czartoski et al. | |

(Continued)

FOREIGN PATENT DOCUMENTS

| | | |
|---|---|---|
| EP | 2782511 A1 | 10/2014 |
| WO | 2005096977 A1 | 10/2005 |
| WO | 2021226241 A1 | 11/2021 |

OTHER PUBLICATIONS

Extended European Search Report issued in Appln. No. 23169772.3 mailed Sep. 18, 2023 (9 pages).

*Primary Examiner* — Eduardo C Robert
*Assistant Examiner* — Christina Negrellirodriguez
(74) *Attorney, Agent, or Firm* — Lerner David LLP

(57) ABSTRACT

A fracture fixation system includes a bone nail configured to be inserted into a canal of a bone by insertion through a distal end of the bone, such that the first end of the bone nail is configured to be seated in a proximal end portion of the bone. The fixation system further includes a bone plate defining an inner surface and an outer surface. The inner surface of the bone plate is configured to abut a lateral surface adjacent the proximal end portion of the bone. The fixation system further includes a first bone screw configured to pass through a first opening defined by the bone plate and a first opening defined by a first portion of the bone nail adjacent the first end of the bone nail to secure the bone plate and the bone nail together.

18 Claims, 4 Drawing Sheets

(56) References Cited

U.S. PATENT DOCUMENTS

| | | | | |
|---|---|---|---|---|
| 2007/0219636 | A1* | 9/2007 | Thakkar | A61B 17/1721 623/18.11 |
| 2007/0233100 | A1 | 10/2007 | Metzinger | |
| 2008/0140077 | A1 | 6/2008 | Kebaish | |
| 2009/0177240 | A1 | 7/2009 | Perez | |
| 2011/0295255 | A1* | 12/2011 | Roberts | A61B 17/746 606/64 |
| 2019/0015138 | A1 | 1/2019 | Schwardt et al. | |
| 2019/0380752 | A1* | 12/2019 | Ferrero Manzanal | A61B 17/744 |

* cited by examiner

RETROGRADE NAIL WITH BONE PLATE

CROSS-REFERENCE TO RELATED APPLICATIONS

The present application claims the benefit of the priority of U.S. Provisional Application 63/334,855 filed Apr. 26, 2022, the disclosure of which is hereby incorporated by reference herein in its entirety.

BACKGROUND OF THE INVENTION

The present invention relates to orthopedic surgical devices used to join and promote healing of fractured bone, and more particularly, and not by limitation, devices used to fixate proximal femoral fractures.

The surgical treatment of femoral neck fractures utilizing internal fixation remains challenging, especially for dislocated unstable fractures. There are a variety of devices used to treat fractures of the femur, humerus, tibia, and other long bones. For example, fractures of the femoral neck, head, and intertrochanteric region have been successfully treated with a variety of internal fixation means such as compression screw assemblies.

Problems may result from weakened or poor-quality bone that is adjacent to the fracture site. Often times the bone adjacent to the fracture is weak and is prone to damage when exposed to compression. For example, there could be uncontrolled shortening of the femoral head when the femoral head compresses towards or into the fracture site. In extreme cases, uncontrolled shortening may cause the femoral head to be compressed all the way into the trochanteric region of the femur. In some cases using intramedullary nails and lateral plates, the proximal nail entry portal may not be accessible or may not provide any means of implant support, and/or comminution of the lateral wall may not allow a proper and mechanically sound placement of the lateral plate with sufficient *varus* prevention.

Attempts to treat such kinds of fractures with above-mentioned methods often result in non-unions, *varus* malalignments, and/or hardware failures including secondary loss of fixation which requires revision surgery. Hardware failures can be significantly more common when using proximal lateral femoral plates as a fixation method. A highly complex and unstable fracture situation with limited or lack of bony support often associated with poor bone quality may limit the primary fixation stability. Due to the intended plate's concept to span the comminuted fracture zone, plate failures often occur within the sub-trochanteric regions representing the highest stresses within the implant's cross-section.

Thus, it would be desirable to provide a fracture fixation system to improve on the prior art disadvantages.

BRIEF SUMMARY OF THE INVENTION

Described herein is a fracture fixation system as applied to a long bone, e.g., a femur, to treat a femoral fracture on a proximal portion of the femur. The fracture fixation system includes a bone plate adapted to be mounted to a lateral exterior surface of the femur near a proximal end of the femur. The bone plate may be a small plate covering only a small portion of the femur near the proximal end, or may alternatively extend along the lateral surface of the femur toward the distal end of the femur, e.g., one quarter, halfway, three quarters, etc. of the length of the femur toward the distal end.

The fracture fixation system further includes a bone nail configured to be inserted into the intramedullary canal of the femur. The bone nail extends from a first distal end to a second proximal end, and the bone nail is configured to be grasped at the proximal end to be inserted into a distal end of the femur with the distal end of the bone nail leading and the proximal end trailing. As such, after the bone nail is inserted into the femur, the first distal leading end of the bone nail is configured to be seated near or within the proximal end portion of the femur, and the second proximal trailing end of the bone nail is configured to be seated relatively nearer the distal end portion of the femur. Such a configuration avoids inserting the bone nail through the fractured end of the femur to avoid causing further damage to the fracture or anchoring the fixation system in a relatively weaker part of the bone.

The distal end of the bone nail has a distal end portion define by two opposing flattened surfaces each having a width. As the bone nail extends proximally from the distal end portion, the width of the bone nail tapers inwardly and the bone nail has a cylindrical middle portion with a diameter smaller than the width of the distal end. In some examples, the opposing flattened surfaces of the distal end may be parallel and symmetric to one another. In other examples, the flattened surfaces of the distal end may define an angled plane relative to the longitudinal axis of the bone nail such that the depth of the bone nail tapers as the bone nail extends distally from the cylindrical middle portion. The distal end of the bone nail further defines screw holes between the flattened surfaces adapted to receive fixation screws.

The fixation system further includes fixations screws configured to be inserted into the bone plate, the femur, and/or the bone nail. That is, some fixation screws may be inserted into screw holes defined by the bone plate and extend into the femur. Other fixation screws may be inserted into screw holes defined by the bone plate, extend into the femur, further passed through the screw holes defined by the distal end of the bone nail, and extended farther into the femur. The proximal end of the bone nail may be shaped to be engaged or mated with an insertion instrument for a controlled implantation of the bone nail into the femur.

According to a first aspect of the disclosure, a fracture fixation system includes a bone nail extending from a first end to a second end, the bone nail configured to be inserted into a canal of a bone by insertion through a distal end of the bone, such that the first end of the bone nail is configured to be seated in a proximal end portion of the bone adjacent a proximal end of the bone opposite the distal end of the bone. The fracture fixation system further includes a bone plate defining an inner surface and an outer surface, the inner surface of the bone plate configured to abut a lateral surface of the bone adjacent the proximal end portion of the bone, and a first bone screw configured to pass through a first opening defined by the bone plate and into the bone.

Further to the fracture fixation system according to the first aspect of the disclosure, the first bone screw may extend from the bone plate such that the first bone screw forms an angle measuring approximately 95 degrees with respect to an axis along which the lateral surface of the bone extends. The bone may be a femur and a distal portion of the first bone screw may be configured to be positioned within a head of the femur. The first bone screw may be configured to pass through a first opening defined by a first portion of the bone nail adjacent the first end of the bone nail to secure the bone plate and the bone nail together. The first portion of the bone nail may define a first flattened surface defined by a first plane. The first portion of the bone nail may define a second flattened surface opposite the first flattened surface, the second flattened surface extending along a second plane substantially parallel to the first plane. The first portion of the bone nail may define a second flattened surface opposite the first flattened surface, the second flattened surface extending along a plane transverse to the first plane. The first and second flattened surfaces may form a taper on the first portion of the bone nail. The first plane may form an angle between 0 and 30 degrees with an axis along which the bone nail extends. The second plane may form an angle between 0 and 30 degrees with an axis along which the bone nail extends. A second portion of the bone nail may extends from the first portion toward the second end of the bone nail, the second portion being generally cylindrical and defining a maximum diameter. The first flattened surface may define a maximum width greater than the maximum diameter of the second portion. The bone may be a femur and the first portion of the bone nail may be configured to be seated in or adjacent a neck of the femur. The fracture fixation system may further include a second bone screw configured to pass through a second opening defined by the bone plate and a second opening defined by the first portion of the bone nail.

According to a second aspect of the disclosure, a method of using a fracture fixation system includes drilling a first bore through a distal end of a bone into a canal of the bone; inserting a bone nail into the first bore, the bone nail extending from a first end to a second end, wherein the first end of the bone nail is inserted into the first bore and into the canal to be seated in a proximal end portion of the bone adjacent a proximal end of the bone opposite the distal end of the bone; positioning a bone plate to abut a lateral surface of the bone adjacent the proximal end portion of the bone; drilling a second bore into the proximal end portion of the bone; and inserting a first bone screw through a first opening defined by the bone plate, into the second bore in the bone, and through a first opening defined by a first portion of the bone nail.

Further to the method of the second aspect of the disclosure, inserting the bone nail into the first bore may include seating the first end of the bone nail within a proximal end portion of the bone such that a portion of the bone separates the first end of the bone nail from the proximal end of the bone. Inserting the first bone screw through the first opening defined by the bone plate may include angling the first bone screw approximately 95 degrees with respect to a plane along which the lateral surface of the bone extends. The method may further include drilling a third bore into the proximal end portion of the bone; and inserting a second bone screw through a second opening defined by the bone plate, into the third bore in the bone, and through a second opening defined by the first portion of the bone nail. The bone may be a femur and inserting the first bone screw may include positioning a distal end of the first bone screw within a head of the femur. Positioning the bone plate to abut the lateral surface of the bone may include aligning the bone plate along the proximal end portion of the bone such that the first opening defined by the bone plate and the first opening defined by the first portion of the bone nail are positioned along a single axis.

DETAILED DESCRIPTION

The present disclosure describes a fracture fixation system, preferably for a femoral fracture (e.g., femoral neck fractures), which includes a retrograde-inserted intramedullary bone nail to utilize the stability of a non-fractured femoral region as a mechanical foundation. The retrograde insertion of the bone nail uses an intact entry portal rather than inserting the bone nail near the fracture region. It should be understood that the fracture fixation system described herein may be applied to long bones in general, and while directed to a femur in the present description, it may also be directed to a humerus, tibia and other long bones.

As used herein, the term "proximal," when used in connection with a device or components of a device, refers to the end of the device closer to the user of the device (e.g., surgeon or operator) when the device is being used as intended. On the other hand, the term "distal," when used in connection with a device or components of a device, refers to the end of the device farther away from the user (e.g., surgeon or operator) when the device is being used as intended. As used herein, the term "superior" refers to an upward direction on the page or relative to an anatomy of a person standing upright. On the other hand, the term "inferior" refers to a downward direction on the page or relative to an anatomy of a person standing upright. It should be understood that these terms are not limiting, but merely used for ease of description, and that varied orientations may cause directions to differ. As used herein, the terms "substantially, "generally," "approximately" and "about" are intended to mean that slight deviations from absolute are included within the scope of the term so modified.

Figure 1:
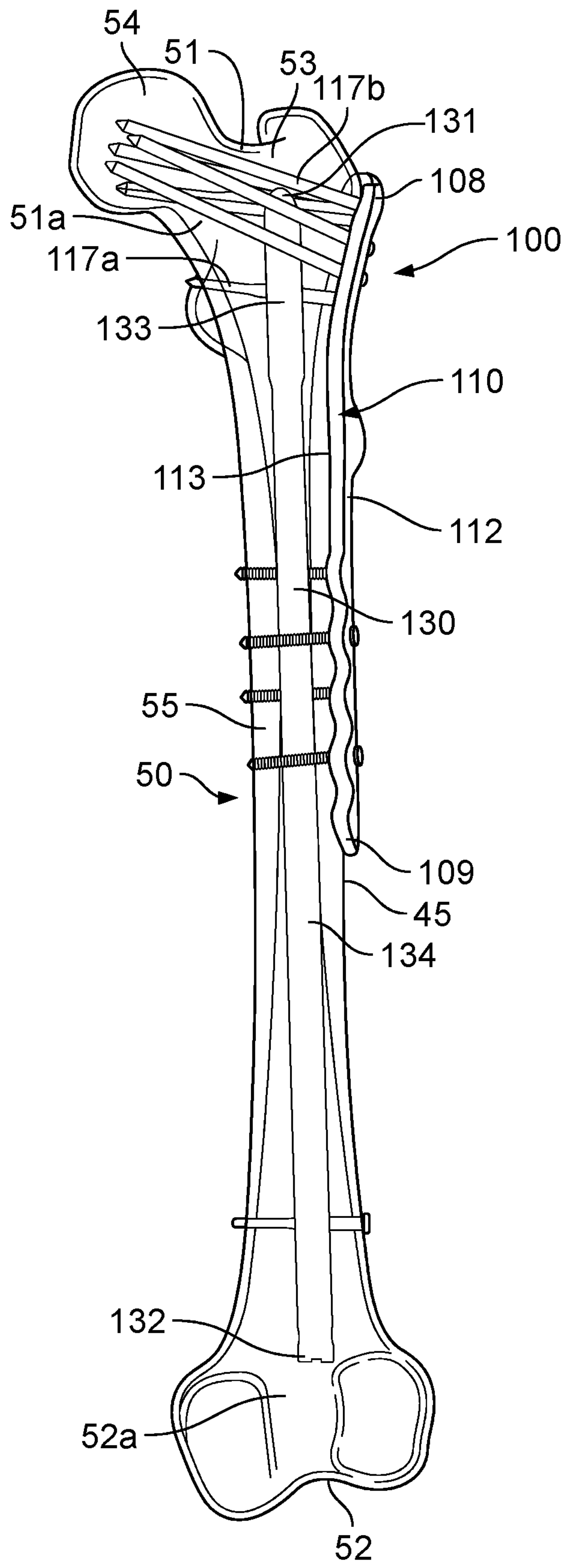
FIG. 1 is a schematic front view of a fracture fixation system applied to a femur according to an embodiment of the disclosure.
Figure 2:
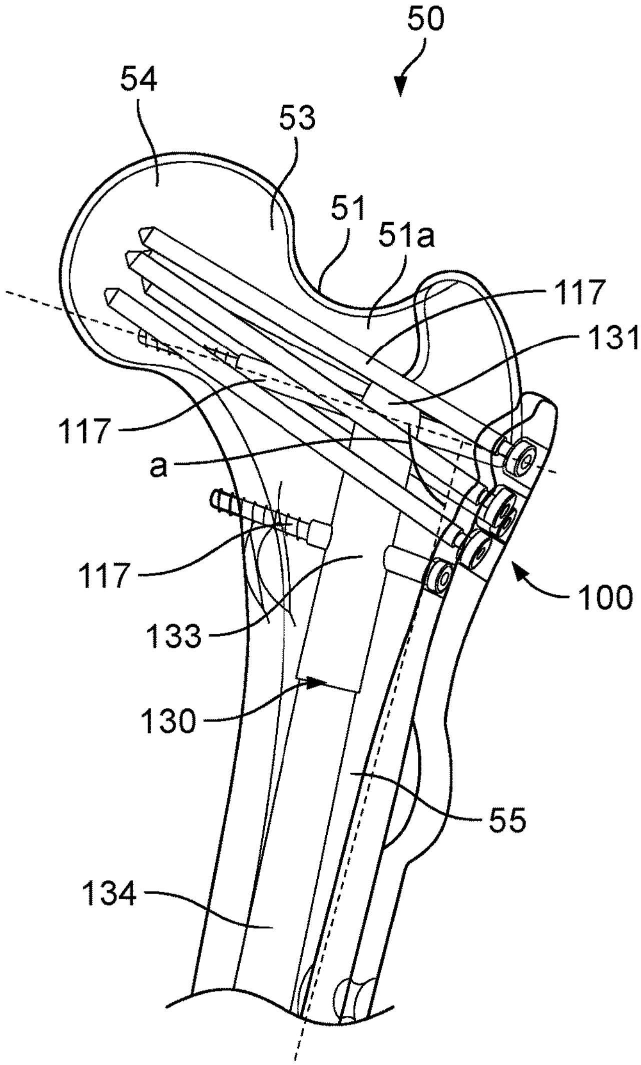
FIGS. 2-3 are schematic front and side views, respectively, of a portion of the fracture fixation system of FIG. 1 on a proximal portion of a femur.
Figure 3:
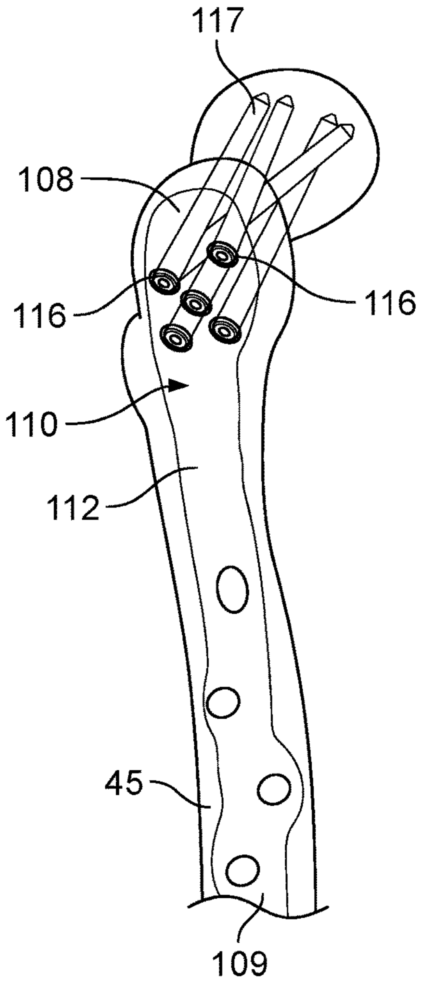

FIGS. 1-3 illustrate a fracture fixation system 100 according to an embodiment of the disclosure. Fracture fixation system 100 includes a plate 110 and a bone nail 130. Plate 110 and bone nail 130 are both shown in FIGS. 1 and 2, however, it is noted that bone nail 130 is not shown in FIG. 3, which focuses on illustration of plate 110. The omission of d bone nail 130 in FIG. 3 is merely for ease of illustration, and it should be understood that fixation system 100 includes both plate 110 and bone nail 130 as shown in FIGS. 1 and 2. Plate 110 has an outer surface 112 spaced from an inner surface 113, which can be placed against a lateral exterior surface 45 of femur 50 as shown in FIG. 1. The positioning of plate 110 ensures an adequate load-sharing between femur 50 and fixation system 100, thus limiting the mechanical stresses on fixation system 100 and reducing chance of failure. The internal fixation of plate 110 and bone nail 130 is designed for positioning at a proximal end portion 51*a* of femur 50 such that in use, plate 110 is disposed at an outer lateral surface 45 on the trochanter of femur 50 and is affixed to bone nail 130 by fixation screws 117. Plate 110 defines at least one, and preferably a plurality, of screw holes 116 therethrough extending from outer surface 112 to inner surface 113 (e.g., the surface adapted to abut the exterior surface of femur 50), each screw hole 116 configured to receive a fixation screw 117, which may be threaded. Screw holes 116 are generally located nearer to a first or superior end 108 of plate 110 than to an opposed second or inferior end 109 of plate 110. In some examples, this allows the second inferior end of plate 110 to extend down the shaft of femur 50 for additional fixation. Fixation screws 117 are inserted through respective screw holes 116 of plate 110 and into femur 50 to couple plate 110 to bone nail 130 and anchor plate 110 securely to femur 50. Plate 110 may optionally include screw holes near inferior end 109 to receive additional fixation screws 117 for further fixation. In other examples, plate 110 may be smaller than what is shown in FIG. 1, such that plate 110 is generally isolated to only proximal end portion 51*a* of femur 50 and does not extend along lateral surface 45 of femur 50 beyond the trochanteric region.

Bone nail 130 extends from a first end 131 to a second end 132, having a first end portion 133 and a second middle portion 134. In the illustrated example, after bone nail 130 is implanted in femur 50, first end 131 (which is the leading end inserted into the femur) is a distal end of bone nail 130 and second end 132 (which is the trailing end inserted into the femur) is a proximal end of bone nail 130 as it is the end nearest the surgeon or operator being grasped and used to manipulate bone nail 130 as bone nail 130 is inserted into femur 50. First end portion 133 is adjacent first end 131, second middle portion 134 is relatively nearer second end 132, and thus, first end portion 133 is positioned more distally in femur 50 relative to second middle portion 134, but nearer proximal end 51 of femur 50.

Figure 4:
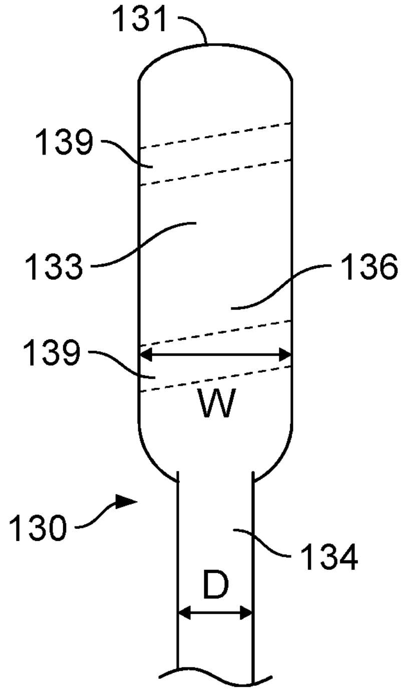
FIGS. 4-5 are schematic front and side views, respectively, of a bone nail of the fracture fixation system of FIG. 1.
Figure 5:
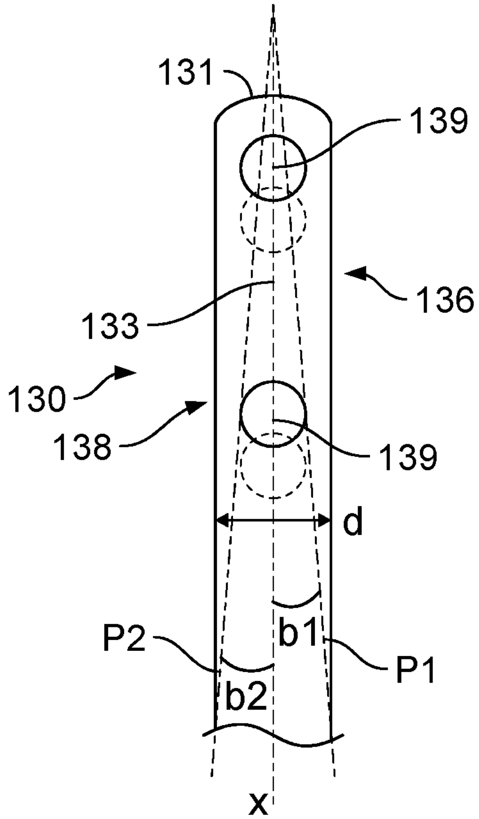

Bone nail 130 is generally paddle-shaped as shown in FIGS. 2 and 4. That is, second portion 134 is generally elongate and cylindrical defining a maximum diameter D. First portion 133, which is shown more clearly in FIGS. 4-5, has a first flat or flattened face or surface 136 defining a width W which is greater than the maximum diameter D of second portion 134. Thus, the width of bone nail 130 tapers as first portion 133 transitions to second portion 134. First portion 133 further includes a second flat or flattened face or surface 138 positioned opposite first flattened face 136, giving at least first and second portions 133, 134 of bone nail 130 the general shape of a paddle. First flattened face 136 is defined by a first plane and second flattened face 138 is defined by in a second plane. In other words, faces 136 and 138 are themselves planar over at least a portion of their surfaces, and in some cases over their entire surfaces. In the example shown, the first and second planes are parallel. In other embodiments, the first and second planes may intersect or extend transverse to one another, as shown by dotted lines P1 and P2 in FIG. 5. For example, first portion 133 extends along a central axis or midline X, and the first plane (along which first flattened face 136 lies), second plane (along which second flattened face 138 lies), or both first and second planes may form an angle with axis X between about 0 degrees and about 30 degrees. In such examples, the depth d of first portion 133 as shown in FIG. 5 may taper as first portion 133 extends superiorly or away from second portion 134. That is, in some examples, the first plane P1 may intersect and form an angle b1 with axis X while the second plane may extend parallel to axis X. In other examples, the first plane may extend parallel to axis X while the second plane P2 may intersect and form an angle b2 with axis X. In further examples, the first and second planes P1, P2 may both intersect with axis X (and each other) and form approximately the same or different angles b1, b2, respectively, with axis X.

Bone nail 130 is configured to be inserted into femur 50 in a retrograde manner. That is, first end 131 is inserted into distal end 52 of femur 50, and bone nail 130 is passed through intramedullary canal 55 of femur 50 until first end 131 and first portion 133 are generally seated in or near proximal end portion 51*a* of femur 50. In the implanted position, first portion 133 of bone nail 130 may be seated in or adjacent to femoral neck 53. First end 131 of bone nail 130 does not fully reach or protrude from proximal end 51 of femur 50. As shown in FIGS. 1-2, a portion of bone separates first end 131 of bone nail 130 from the proximal-most end 51 of proximal end portion 51*a* of femur 50. Distal insertion of bone nail 130 may reduce the number of holes to be drilled on proximal end portion 51*a* of femur 50 for revision, keeping more of the original bone intact and thereby improving stability and strength of the fractured femur during healing.

First portion 133 of bone nail 130 further defines apertures 139 extending generally along the width W of first portion 133 surrounded by first and second flattened faces 136, 138 as shown in FIG. 5. Apertures 139 are sized, shaped and positioned to receive fixation screws 117 to couple bone nail 130 to plate 110 and secure fracture fixation system 100 to femur 50. In the illustrated example, first portion 133 of bone nail 130 includes two apertures 139 adapted to each receive a fixation screw 117. Fixation system 100 may optionally include additional fixation screws 117 extending through screw holes 116 on plate 110 without extending through apertures 139 of bone nail 130, e.g., extending through femur 50 alongside and without contacting bone nail 130 rather than through bone nail 130 as shown in FIG. 1. For example, fixation screw 117*a* extends through both plate 110 and bone nail 130, whereas fixation screw 117*b* extends only through plate 110. Fixation screws 117 may be inserted into screw holes 116 of plate 110 at a particular angle a to optimize the stability of femur 50 after implantation of fracture fixation system 100. For example, a fixation screw 117 may extend into proximal end portion 51*a* of femur 50 at angle a measuring about 95 degrees relative to lateral surface 45 of femur 50. In other words, a fixation screw 117 may extend along a first axis, and the lateral exterior surface 45 of femur 50 may define a second axis (both axes shown in dotted lines in FIG. 2). Fixation screw 117 may be inserted such that angle a between 90 and 100 degrees, preferably 95 degrees, is formed between the first and second axes. Such an angle will target the best bone quality of femoral head 54 to ensure reliable screw anchorage.

Figure 6:
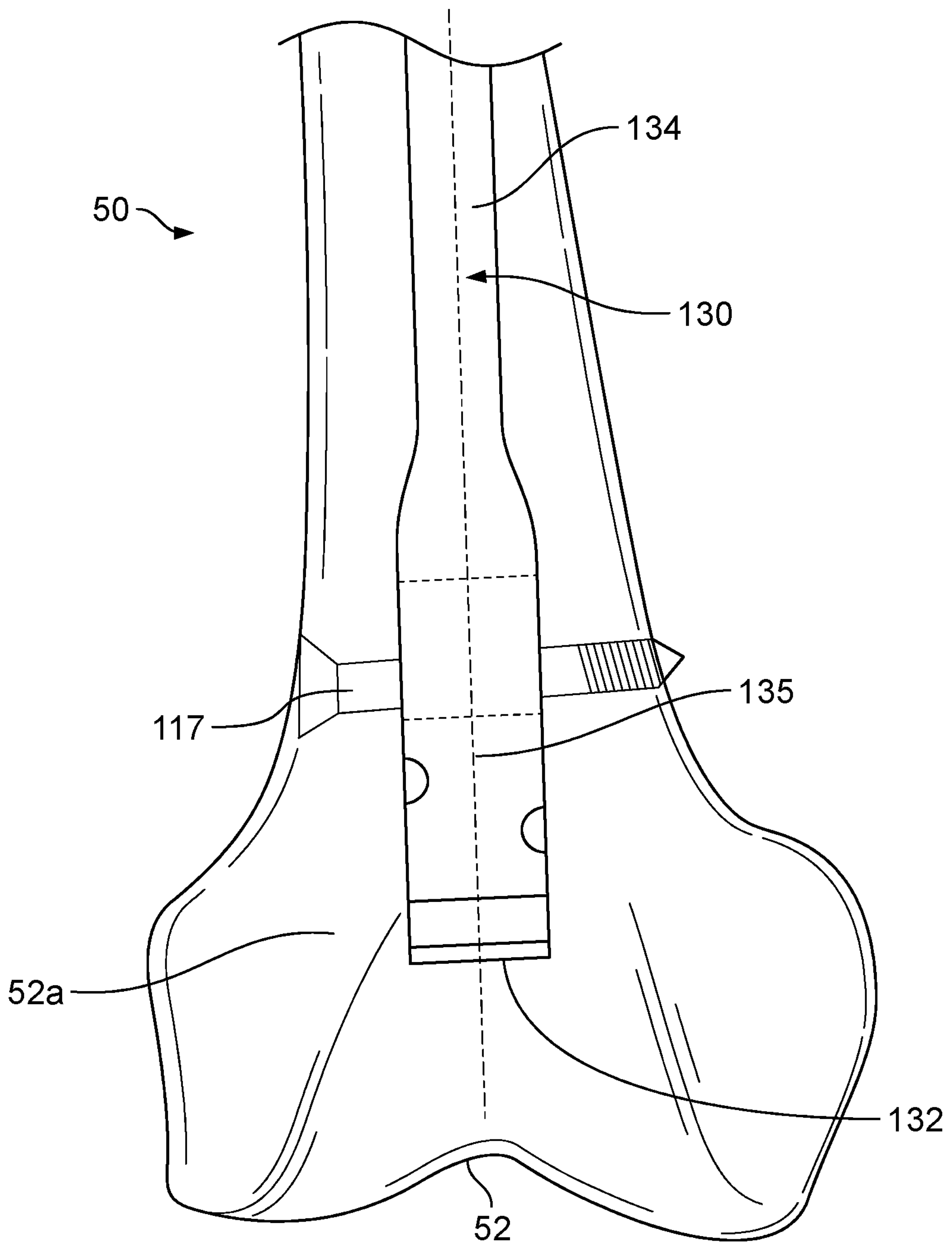
FIG. 6 is a schematic front view of a portion of a fracture fixation system according to another embodiment of the disclosure on a distal portion of a femur.

In some examples, second portion 134 of bone nail 130 may extend fully to second end 132 of bone nail 130 (e.g., all the way to the true distal/inferior end of the bone nail), with second end 132 having a cylindrical shape. In other examples, bone nail 130 may include a third end portion 135 opposite first end portion 133 which may have a substantially cylindrical shape, as shown in FIG. 6. Third end portion 135 may be adapted to be seated in a distal end portion 52*a* adjacent distal end 52 of femur 50. Third end portion 135 may also define an aperture extending therethrough along the width of third end portion 135, the aperture adapted to receive a fixation screw 117 to secure third end portion 135 to distal end portion 52*a* of femur 50. It is contemplated that third end portion 135, whether it is cylindrical, paddle-shaped, etc., may be sized and shaped to receive or mate with an insertion device for handling, manipulation and insertion of bone nail 130 by a surgeon or operator. For example, third end portion 135 may define at least one recess, indentation, protrusion, clasp, latch, etc., or define a generally flattened shape conducive to being grasped, engaged or coupled to an insertion instrument, or the third end portion may include a combination of any of the above.

Fracture fixation system 100 may be manufactured based on patient-specific data to a particular size, shape, and profile, which may aid in effectively controlling *varus* forces.

A method of using fracture fixation system 100 described above includes a first step of drilling a bore hole through intramedullary canal 55 starting at distal end 52 of femur 50. Next, at least one bore hole is drilled into femoral neck 53 and optionally into femoral head 54. The number of bore holes drilled into femoral neck 53 corresponds to the number of threaded fixation screws 117 that will be inserted through plate 110. Bore holes drilled through femoral neck 53 may also be used for viewing and alignment of bone nail 130 inside femur 50. A bore hole may also optionally be drilled through distal end portion 52*a* across femur 50 to receive an additional fixation screw 117.

First end 131 of bone nail 130 is inserted into distal end 52 of femur 50 and passed through intramedullary canal 55 until first end 131 is seated in proximal end portion 51*a* of femur 50, which is in or adjacent femoral neck 53. Plate 110 is mounted to femur 50, including placing inner surface 113 of plate 110 against an exterior surface 45 of femur 50. Plate 110 is generally positioned on or adjacent the trochanter of femur 50 so that screw holes 116 defined by plate 110 align with corresponding apertures 139 defined by first portion 133 of bone nail 130. One or more fixation screws 117 may then be inserted through some or all of screw holes 116 of plate 110, into femoral neck 53 and through apertures 139 of first portion 133 of bone nail 130. It is contemplated that some or all of threaded fixation screws 117 may extend through femoral neck 53 and into femoral head 54. It is also contemplated that some or all of fixation screws 117 may extend only through femoral neck 53 without contacting bone nail 130. Finally, one or more fixation screws 117 may be inserted through distal end portion 52*a* of femur 50 and through third portion 135 of bone nail 130 to further secure bone nail 130 within femur.

In certain embodiments where the bone nail may be inserted through the proximal end of the femur, the method is substantially similar to the method described above, but performed on the opposite ends of the femur. That is, the bore is drilled through the proximal end of the femur and through intramedullary canal to prepare for insertion of the bone nail through the proximal end of the femur. Bore holes are drilled across the distal end of the femur to prepare for insertion of the threaded fixation screws. The distal end of the bone nail is inserted into the proximal end of the femur and passed through the intramedullary canal of the femur. The bone plate is mounted to a distal end of the femur so that the screw holes of the bone plate are aligned with the screw holes of the bone nail. Finally, the threaded fixation screws are inserted through the bone plate, through the femur, and through the bone nail to secure both the bone nail and the bone plate to the femur. Similarly, a bore may also be drilled across the proximal end of the femur and a fixation screw inserted through the proximal bore and a proximal end of the bone nail to further secure the bone nail to the femur. Such embodiments may be used when a fracture occurs at the distal end of the femur and the bone quality is poor, thereby resulting in an infeasible entry portal at the distal end of the femur. Avoiding insertion of the bone nail through the fractured end of the femur is a critical aspect of all embodiments of the present application to preserve bone quality and promote stability of the fracture fixation system.

Each component of system 100, including all of the screws, can be made of any surgical grade rigid material such as plastic, ceramic, or metal, and particularly various metals such as titanium, titanium alloys, stainless steel, cobalt chrome alloys, tantalum and niobium, or any combination thereof. Gold and/or silver can be provided in the material composition or as a coating of a component.

Each component of system 100, including all of the screws, may be formed by an additive manufacturing process, including but not limited to electron beam melting (EBM), selective laser sintering (SLS), selective laser melting (SLM), binder jet printing, and blown powder fusion for use with metal powders. Any of the components can be manufactured by 3D printing.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A fracture fixation system, comprising:

a bone nail extending from a first end to a second end, the bone nail configured to be inserted into a canal of a bone by insertion through a distal end of the bone, such that the first end of the bone nail is configured to be seated in a proximal end portion of the bone adjacent a proximal end of the bone opposite the distal end of the bone;

a bone plate defining an inner surface and an outer surface, the inner surface of the bone plate configured to abut a lateral surface of the bone adjacent the proximal end portion of the bone;

a first bone screw configured to pass through a first opening defined by the bone plate and into a neck of the bone, wherein a central longitudinal axis of the first bone screw is spaced from the bone nail.

2. The fracture fixation system of claim 1, wherein the first bone screw extends from the bone plate such that the first bone screw forms an angle measuring approximately 95 degrees with respect to an axis along which the lateral surface of the bone extends.

3. The fracture fixation system of claim 1, wherein the bone is a femur and a distal portion of the first bone screw is configured to be positioned within a head of the femur.

4. The fracture fixation system of claim 1, wherein a first portion of the bone nail defines a first flattened surface defined by a first plane.

5. The fracture fixation system of claim 4, wherein the first portion of the bone nail defines a second flattened surface opposite the first flattened surface, the second flattened surface extending along a second plane substantially parallel to the first plane.

6. The fracture fixation system of claim 4, wherein the first portion of the bone nail defines a second flattened surface opposite the first flattened surface, the second flattened surface extending along a plane transverse to the first plane.

7. The fracture fixation system of claim 6, wherein the first and second flattened surfaces form a taper on the first portion of the bone nail.

8. The fracture fixation system of claim 6, wherein the first plane forms an angle between 0 and 30 degrees with an axis along which the bone nail extends.

9. The fracture fixation system of claim 6, wherein the second flattened surface defines a second plane that forms an angle between 0 and 30 degrees with an axis along which the bone nail extends.

10. The fracture fixation system of claim 4, wherein a second portion of the bone nail extends from the first portion toward the second end of the bone nail, the second portion being generally cylindrical and defining a maximum diameter.

11. The fracture fixation system of claim 10, wherein the first flattened surface defines a maximum width greater than the maximum diameter of the second portion.

12. The fracture fixation system of claim 1, wherein the bone is a femur and the first end of the bone nail is configured to be seated in or adjacent a neck of the femur.

13. The fracture fixation system of claim 1, further comprising a second bone screw configured to pass through a second opening defined by the bone plate and an opening defined by the bone nail.

14. A method of using a fracture fixation system, comprising:

drilling a first bore through a distal end of a bone into a canal of the bone;

inserting a bone nail into the first bore, the bone nail extending from a first end to a second end, wherein the first end of the bone nail is inserted into the first bore and into the canal to be seated in a proximal end portion of the bone adjacent a proximal end of the bone opposite the distal end of the bone;

positioning a bone plate to abut a lateral surface of the bone adjacent the proximal end portion of the bone;

drilling a second bore into the proximal end portion of the bone;

inserting a first bone screw through a first opening defined by the bone plate, into the second bore in the bone, and through a first opening defined by a first portion of the bone nail;

drilling a third bore into the proximal end portion of the bone, the third bore extending along an axis spaced apart from the bone nail; and inserting a second bone screw through a second opening defined by the bone plate and into the third bore in the bone.

15. The method of claim 14, wherein inserting the bone nail into the first bore includes seating the first end of the bone nail within a proximal end portion of the bone such that a portion of the bone separates the first end of the bone nail from the proximal end of the bone.

16. The method of claim 14, wherein inserting the first bone screw through the first opening defined by the bone plate includes angling the first bone screw approximately 95 degrees with respect to a plane along which the lateral surface of the bone extends.

17. The method of claim 14, wherein the bone is a femur and inserting the first bone screw includes positioning a distal end of the first bone screw within a head of the femur.

18. The method of claim 14, wherein positioning the bone plate to abut the lateral surface of the bone includes aligning the bone plate along the proximal end portion of the bone such that the first opening defined by the bone plate and the first opening defined by the first portion of the bone nail are positioned along a single axis.

* * * * *